(12) United States Patent
Wang et al.

(10) Patent No.: US 10,149,479 B1
(45) Date of Patent: Dec. 11, 2018

(54) PREPARATION METHOD AND USE OF AN ATOMIC-STATE FLUID IODINE AND ITS DERIVED NANO-IODINE

(71) Applicant: Chinese Academy of Agricultural Engineering, Beijing (CN)

(72) Inventors: Shikui Wang, Beijing (CN); Zhiqing Tian, Beijing (CN); Liang Liang, Beijing (CN); Xuefang Hu, Beijing (CN); Zhimin Zhang, Beijing (CN)

(73) Assignee: Chinese Academy of Agricultural Engineering, Beijing (CN)

( * ) Notice: Subject to any disclaimer, the term of this patent is extended or adjusted under 35 U.S.C. 154(b) by 0 days.

(21) Appl. No.: 15/631,905

(22) Filed: Jun. 23, 2017

(30) Foreign Application Priority Data

May 27, 2017 (CN) .......................... 2017 1 0388396

(51) Int. Cl.
| | | |
|---|---|---|
| *A01N 59/12* | (2006.01) | |
| *A61K 8/20* | (2006.01) | |
| *A61Q 17/00* | (2006.01) | |
| *C01B 7/14* | (2006.01) | |
| *A01N 25/02* | (2006.01) | |

(52) U.S. Cl.
CPC ............ *A01N 59/12* (2013.01); *A01N 25/02* (2013.01); *A61K 8/20* (2013.01); *A61Q 17/005* (2013.01); *C01B 7/14* (2013.01)

(58) Field of Classification Search
None
See application file for complete search history.

(56) References Cited

U.S. PATENT DOCUMENTS

| | | |
|---|---|---|
| 4,345,049 A | 8/1982 | Walter et al. |
| 7,195,772 B2 | 3/2007 | Zeng et al. |

FOREIGN PATENT DOCUMENTS

| | | |
|---|---|---|
| CN | 1 207 271 | 6/2005 |
| DE | 2 941 387 | 5/1981 |
| DE | 3 060 935 | 11/1982 |

*Primary Examiner* — Susan T Tran
(74) *Attorney, Agent, or Firm* — Morrison & Foerster LLP

(57) ABSTRACT

In one aspect, the present disclosure belongs to the new material field and can be used to produce atomic-state fluid iodine by iodine atom rearrangement occurring in the pseudo-critical reaction system. In one aspect, the atomic-state fluid iodine has a specific gravity of about 3.8-4.0 g/mL and maintains stable physical state under 10-100 C and light environment without sublimation or decomposition. As a new-type iodine-structural material, atomic-state fluid iodine and atomic-state nano-iodine can be used as the $4^{th}$ generation of atomic-state iodine disinfectant for human, animal and living environment, experimental data show that as atomic-state germicide in agricultural production, it can prevent and cure specific parasitism disease of plant, such as Citrus Huanglongbing and citrus bacterial canker disease, banana panama disease, fruit tree branch blight disease and plant virus disease, and it can also be used as a substitution in medical and health field for its features of safety, stability and high potency.

8 Claims, 4 Drawing Sheets

Figure 1:
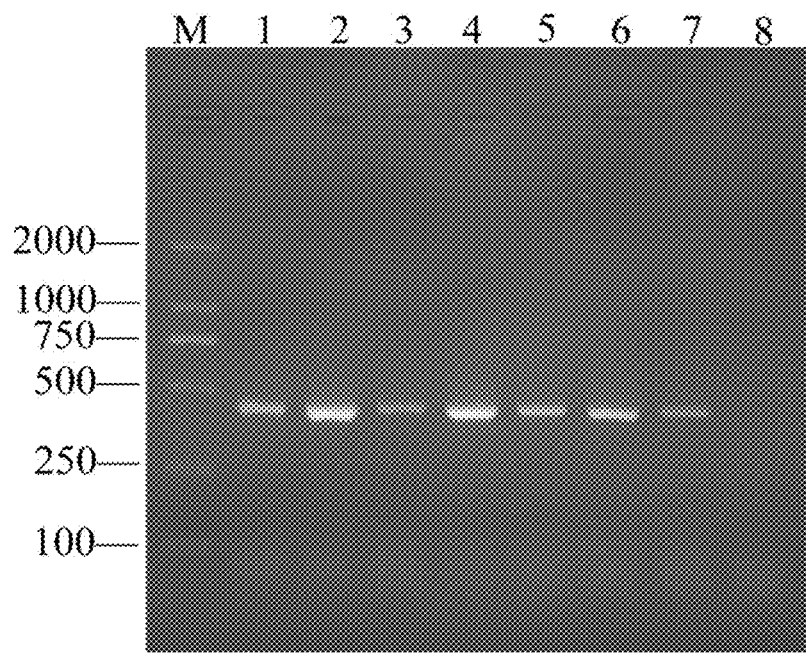

PREPARATION METHOD AND USE OF AN ATOMIC-STATE FLUID IODINE AND ITS DERIVED NANO-IODINE

CROSS-REFERENCE TO RELATED APPLICATIONS

This application claims benefit of priority to Chinese Patent Application No. CN201710388396.5, filed on May 27, 2017, the content of which is incorporated herein by reference in its entirety for all purposes.

TECHNICAL FIELD

The present disclosure relates to the new material field and, in particular aspects, describes a preparation method and use of an atomic-state fluid iodine and its derived nano-iodine that can be used as agricultural germicide and medical disinfectant.

BACKGROUND

As an active non-metallic material, iodine was first discovered by the French chemist Courtois, B. (1777-1838) in 1811, and has shown its important application values in various fields. Used as a medical disinfectant and agricultural germicide, iodine plays an important role in the disinfection and sterilization in the form of $I_2$ and HOI.

Studies have shown that iodine reacts with pathogens in various ways. Iodine interacts with hydroxyl-, amino-, hydrocarbyl-, and mercapto-groups to affect the survival of microorganisms. After alkaline amino acids (lysine, histidine and arginine) and nucleotide bases (adenine, cytosine and guanine) forming iodine derivatives, their important hydrogen bonds are destroyed and blocked, which causes fatal changes to the corresponding proteins, enzymes and nucleic acids. After a mercapto-group of cysteine is oxidized by iodine, its ability to form disulfide bond loses and protein synthesis is blocked. Cell respiration enzymes lose its activity after its mercapto groups are destroyed. Phenolic groups of tyrosine react with iodine to form monoiodide or diiodide derivatives, and the iodine atoms at ortho position will prevent functions of phenolic hydroxyl groups due to steric hindrance and electronic effect. Iodine can also alter the physical properties and chemical properties of unsaturated fatty acids by destroying carbon-carbon double bonds in its molecules, resulting in irreversible strong bactericidal properties. However, due to iodine's volatility and light instability, its durable effect is poor and efficacy cannot be maintained for a long term, which has largely restricted its use in disinfection and pesticide.

Since its discovery, iodine, as a disinfectant, has experienced 3 generations of developing stages as iodine tincture, iodophor and PVP-I, in the 1980s, the German patents for invention DE-2941387 and DE-3060935 provided polyvinyl pyrrolidone (PVP-I), which is widely recognized and used in the worldwide medical treatment and public health fields. However, due to high cost and effect restrictions, it is not widely used as agricultural disinfectant and germicide. Disclosure in Patents "amino acid complex iodine" (CN1207271C) and iodine oligosaccharide acids (ZL201010288868.8) has extended the application of complex iodine in the fields of agricultural disinfectant (aquaculture disinfectant) and agricultural germicide (control agents for plant virus disease and bacterial disease). The defects in terms of the complex's structural stability and its conductivity and high potency in the plant restrict its application. To stabilize iodine molecules, some stable complex carrier was chosen to prepare stable complex iodine. But temperature required for maintaining complex iodine's stability is basically under 80 C. Instability is still a problem when the complex iodine was put under light condition, which is the biggest obstacle that blocks its application as agricultural germicide. Moreover, in above said complex iodine, to stabilize iodine molecules, a large ratio of complexing carriers is required. This will result in a high product cost and affect efficient function exertion of iodine, weakening its activity.

Until now, iodine disinfectant/germicide product especially suitable for agricultural filed or related literature/report about developing iodine disinfectant/germicide suitable for agricultural filed have not been seen, let alone iodine disinfectant/germicide which can cure and well control specific parasitism disease of plant causing widespread disease in agricultural field, such as Citrus Huanglongbing (HLB or citrus greening disease) and citrus bacterial canker disease, plant virus disease and vascular bundle disease.

SUMMARY

Based on the blank and demand in the abovementioned field, the present disclosure provides an atomic-state fluid iodine product suitable for use in agriculture (agricultural germicide) and medical health (disinfectant for skin and living environment) and its preparation method.

The technical scheme requesting protection goes as follows:

On one hand, the present disclosure provides a method for producing an atomic-state fluid iodine, includes proceeding with following steps in a pseudo-critical reaction system, that is, ordinary pressure and temperature scope close to iodine's boiling point, (1) dispersing solid iodine in solvent, mixing and stirring under 110-200 C for reflux distillation, cooling the liquid produced through said reflux distillation to room temperature, thereafter separating the lower-layer liquid in a delivery flask, wherein said solvent selected from: dimethyl sulfoxide, diphenyl sulfone, triethanolamine, N-methylpyrrolidone, sulfolane, N, N-dimethylformamide, (2) purifying: washing the lower-layer of liquid with distilled water and non-polar solvent to remove water-soluble and ester-soluble substances produced by solvent decomposition, (3) placing the purified lower-layer liquid in a low temperature environment under 10 C solidifying, thereafter removing the upper-layer solution and obtain solid product, placing the said solid product in room temperature environment till the solid product turning into fluid, which is the atomic-state fluid iodine.

In some embodiments, room temperature is the range of temperatures that people prefer for indoor settings, at which the air feels neither hot nor cold when wearing typical indoor clothing. The range is typically between 15° C. (59° F.) and 25° C. (77° F.).

In one aspect, in step (1), said solid iodine is mixed with the solvent with the ratio of 0.1-1.0 g:1.0 mL, such as 0.1 g:1.0 mL, 0.2 g:1.0 mL, 0.3 g:1.0 mL, 0.4 g:1.0 mL, 0.5 g:1.0 mL, 0.6 g:1.0 mL, 0.7 g:1.0 mL, 0.8 g:1.0 mL, 0.9 g:1.0 mL, or 1.0 g:1.0 mL.

In one aspect, in the step (1), stirring and refluxing are performed at a temperature of 110 to 200 C for 3-5 hours. In some embodiments, stirring and refluxing are performed at a temperature of 115-200 C, 120-200 C, 130-200 C, 140-200 C, 150-200 C, 160-200 C, 170-200 C or 180-200 C for 3-5 hours.

In one aspect, in the step (2), the lower-layer of liquid is washed with distilled water and non-polar solvent for 3-8 time and with non-polar solvent for 3-5 times.

In one aspect, the temperature range of the distilled water is from about 10 to about 20 C; the non-polar solvent is selected from petroleum ether, carbon tetrachloride and dichloroethane. In one aspect, the low temperature environment described in step (3) indicates temperature below about 8 C, and in some embodiments, below about 4-8 C.

On the other hand, in one aspect, this invention provides a kind of atomic-state fluid iodide, the atomic-state fluid iodide is prepared by the method of any of the embodiments disclosed herein, and has following characteristics:

it is of solid state with black color and metallic luster under a temperature of below 10° C.;

it is of fluid state with its main body as black color and margin as dark red color, with a specific gravity of about 3.8—about 4.0 g/ml under a temperature of about 10-about 100 C, and it is stable without sublimation under light condition, and it is soluble in methanol, ethanol and other polar organic solvents, and insoluble in water and non-polar organic solvents, and it presents atomic cluster agglutination in the water.

In another aspect, this invention provides a kind of atomic-state nano-iodide, which, as a derivative of the atomic-state fluid iodide, is prepared by adding with polar organic solvent as dispersion medium and followed with mixing and blending, and has following characteristics:

when dispersed in water its diameter range of dispersed particles is about 100-about 300 nm, and when dispersed in the air medium its diameter range of dispersed particles is about 90-about 120 nm.

In one aspect, the abovementioned dispersion medium is selected from one or more of the following: 70-99% ethanol, methanol, acetone, ethylene glycol, propylene glycol, polyvinyl alcohol and polyethylene glycol.

In some embodiments, the dispersion medium is about 70-about 99% ethanol with a dispersion concentration of 1-10%, that is, the volume ratio of fluid iodine to dispersion medium is about (1-10): 100, such as about 1:100, about 2:100, about 3:100, about 4:100, about 5:100, about 6:100, about 7:100, about 8:100, about 9:100, or about 10:100.

In a further aspect, the present disclosure provides a kind of liquid atomic-state nano-iodine, which is obtained by adding the above any one of atomic-state nano-iodine into distilled water with oscillation and dispersion, which can be stably stored at a temperature of about 4 to about 20 C; and in some embodiments, the volume ratio of atomic-state nano-iodine to distilled water is about 0.1-1:100, such as about 0.1:100, about 0.2:100, about 0.3:100, about 0.4:100, about 0.5:100, about 0.6:100, about 0.7:100, about 0.8:100, about 0.9:100, or about 1:100.

Then in a further aspect, the present disclosure provides a solid atomic-state nano-iodine, which is solid part obtained by centrifuging the abovementioned liquid atomic-state nano-iodine at a speed of about 3000-5000 rpm under a low temperature for about 3-8 minutes and can be stably stored at a temperature of about 4 to 8 C.

Based on the abovementioned fluid iodine/nano-iodine, in one aspect, this invention provides a kind of medicine for plant disease, which comprises following ingredients as pharmaceutical activity ingredients:

the abovementioned atomic-state fluid iodine,
the abovementioned atomic-state nano-iodine,
the abovementioned liquid atomic-state nano-iodine, and/or
the abovementioned solid atomic-state nano-iodine, said plant diseases include Citrus Huanglongbing, Citrus bacterial canker disease, banana panama disease, fruit tree branch blight disease and dry rot disease.

Based on the above-mentioned fluid iodine/nano-iodine, this invention also provides a disinfectant, which comprising following ingredients as disinfectant activity ingredients:

the abovementioned atomic-state fluid iodine,
the abovementioned atomic-state nano-iodine,
the abovementioned liquid atomic-state nano-iodine, or
the abovementioned solid atomic-state nano-iodine;

said disinfectant can kill fungus, bacterium and virus.

In one aspect, said fungus, bacterium and virus refer to those parasitic on human skin, living environment, plant tissue, animal body surface and animal breeding environment.

Accordingly, in one aspect, the present disclosure provides the pharmaceutical purpose of the abovementioned atomic-state fluid iodine or atomic-state nano-iodine in terms of preparing a disinfectant or a plant disease control agent, which is characterized with: its active ingredients are based on the atomic-state fluid iodine and atomic-state nano-iodine.

In one aspect, in the abovementioned pharmaceutical purpose, said plant diseases include Citrus Huanglongbing, Citrus bacterial canker disease, banana panama disease, fruit tree branch blight disease and dry rot disease.

Said disinfectant can kill microbes, including fungus, bacterium and virus. In some embodiments, the fungus, bacterium and virus parasitize or can be found in human skin, living environment, plant tissue, animal body surface and animal breeding environment.

This invention also requests to protect a method of preventing and curing plant disease, which is characterized with: to apply the abovementioned control agent to the soil in which plants grow or in related cultivation area.

In one aspect, said plant disease refers to Citrus Huanglongbing, including to apply the control agent to surrounding plants of infected plants.

Based on the boiling point temperature range of iodine, this invention sets up a pseudo-critical reaction system in a certain solvent mediums under normal pressure condition; it is preliminarily estimated that in this system, structure of the iodine atom is rearranged to strengthen van der Waals forces between atoms, and atoms' arrangement alters from square or rectangular lattice into lamellar or disorderly arrangement, resulting in iodine's existence at fluid state at room temperature due to strengthened van der Waals forces, named as the atomic-state fluid iodine.

In one aspect, the present disclosure solves the problem of the light and thermal stability fundamentally of iodine, and exhibits good atomic structure stability at 100 C and long-term light condition, so it has the potential to be applied to wider fields. In one aspect, the present disclosure further combines with nano-technology and prepares atomic-state nano-iodine in polar organic dispersion medium, which can be used as the $4^{th}$ generation of iodine disinfectant for hygiene purpose, for it can well replace iodine tincture, iodophor and PVP-I thanks to its advantages of light and thermal stability, low cost, safety and high potency.

In the field of agricultural germicide, through its special disinfectant mechanism as high-efficiency systemic & tunneling potency and targeted attack generated by quantum mechanics effect of nano particle, atomic-state nano-iodine can create good effects on existing specific parasitism disease of plant causing widespread agricultural disease, such as candidates *liberobacter asiaticum* and citrus bacterial canker disease, plant virus disease and vascular bundle disease. As an atomic-state germicide, it effectively solve the adverse effect on environment, residue problem and pathogen resistance caused by chemical synthetic germicide.

Figure 3:
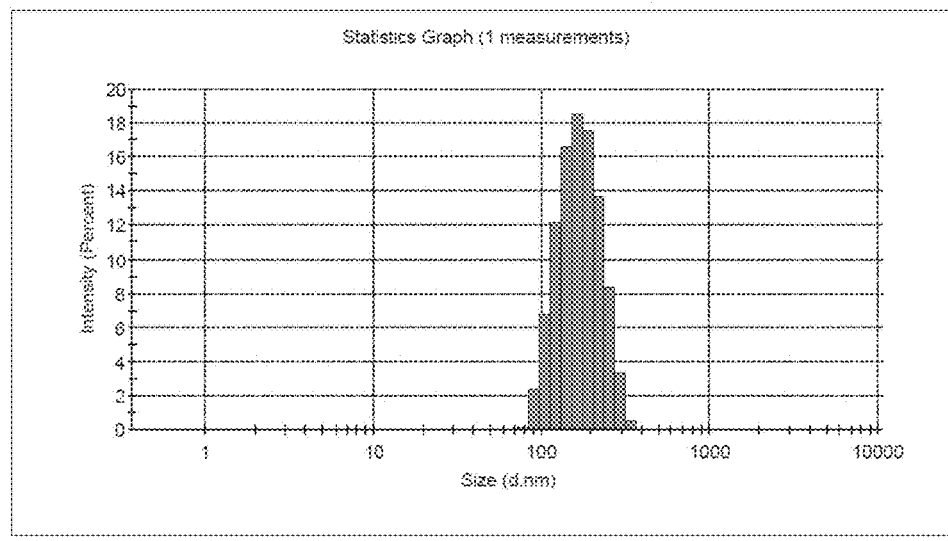

In summary, the new materials, atomic-state fluid iodine and atomic-state nano-iodine included in this invention, have great significance for scientific research and application of iodine.

DESCRIPTION OF PICTURES

FIG. 1 showed the PCR result of sample before being applied atomic-state fluid iodine and nano-iodine to prevent and cure Citrus Huanglongbing in application example No. 1 (control group):

wherein M: D2000 marker; 1: Guangdong Zhuliao sample No. 1; 2: Guangdong Zhuliao sample No. 2; 3: Guangdong Zhuliao sample No. 3; 4. Guangdong Xinhui sample No. 1; 5. Guangdong Xinhui sample No. 2; 6: Guangdong Xinhui sample No. 3; 7: positive control; 8: negative control.

FIG. 2 showed PCR result of sample after being applied atomic-state fluid iodine and nano-iodine to prevent and cure Citrus Huanglongbing in application example No. 1 (experimental group).

Among experimental group (treated) M: D2000 marker. 1, 2: Guangdong Xinhui No. 1 agent-applied citrus trees; 3, 4: Guangdong Xinhui No. 2 agent-applied citrus trees; 5, 6: Guangdong Zhuliao No. 1 agent-applied citrus trees; 7, 8: Guangdong Zhuliao No. 2 agent-applied citrus trees; 9: negative control.

FIG. 3 showed the measuring result for particle diameter of atomic-state nano-iodine, wherein particle diameter standing at 100-300 nm.

FIG. 4 showed a view under an electron microscope, which show that average particle diameter for atomic-state nano-iodine is about 100 nm.

DETAILED DESCRIPTION

The following are examples for preparation scheme, testing method and application effect of atomic-state fluid iodine included in this invention, but shall not be regarded as limitation of protection scope of this invention.

Example 1: Preparation and Test for 50 Grams Atomic-State Fluid Iodine

Material:

Iodine: specifications: solid, AR250 g/bottle, purchased from Tianjin Chemical Reagents Store.

Remaining are ordinary chemical pure grade reagents.

Preparation Steps:

Put 50 g solid iodine into a 250 ml round-bottom flask and add 50 ml dimethyl sulfoxide; heat to 190 C by oil bath, stir and reflux distillation for 3 hours and obtain 30-45 ml liquids, lower-layer of which needs to be separated in delivery flask after being cooling to room temperature; put the separated lower-layer liquid into washing bottle, wash it with 10 C distilled water for 5 times, and then wash with petroleum ether for 3 times, cool it to 5 C, and remove the upper liquid after solidification; under room temperature, the solid will melt into fluid, the atomic-state fluid iodine is obtained, which shall be poured into package bottle for storage, the yield coefficient stands at over 95%, that is, at least 45 g atomic-state fluid iodine can be generated from 50 g iodine.

Product Test

Light and Thermal Stability Test:

Test light stability under sunlight: put 10 g fluid iodine into a 100 ml transparent glass bottle, with a daily sunshine of 6 hours, and observe the fluid iodine overflow every day. It can be proved possessing good light stability if after 10 days no red product appears on the bottle wall.

Water bath method is used for thermal stability test, put 10 g fluid iodine into a 100 ml transparent glass bottle, place the open bottle in 10-100 C constant temperature water, staying in water of different temperatures, e.g., 10, 30, 50, 80 and 100 C, at each temperatures for 1 hour or more, then being tested by starch test paper, if no blue color appears, it can be proved possessing good thermal stability.

Test result shows that the specific gravity for atomic-state fluid iodine stands at 3.8-4.0 g/mL, it exists at fluid state and possesses stable physical condition at 10-100 C and light condition, and no iodine gas overflow is detected.

Parallel Examples

In some parallel examples, diphenyl sulfone, triethanolamine, N-methylpyrrolidone, sulfolane or N, N-dimethylformamide is used as solvent instead of dimethyl sulfoxide, and the results of light and thermal stability test for products obtained are consistent with abovementioned example.

In other parallel examples, the lower-layer liquid is washed with tetrachloride, dichloroethane instead of petroleum ether. The results of light and thermal stability test for products obtained are consistent with abovementioned example.

Then, in other parallel examples, temperatures for oil bath are set as 110, 120, 125, 130, 135, 140, 145, 150, 155, 160, 165, 170, 175, 180, 185, 195 and 200 C respectively.

The results show the product produced with temperature for oil bath rising from 110 to 150 C, the stability of the product gradually increases, and the yield coefficient also gradually increases from about 50% to 70%; and the product was stayed in water of different temperatures, e.g., 10, 30, 50, 80 and 100 C, at each temperatures for 40 minutes, and starch test paper shows blue, which means that thermal stability of product produced under such conditions is weaker than that under 185 C. But there is no difference in terms of light stability.

The products produced with temperature 160-200 C for oil bath, which showed a better thermal stability, staying in water stayed in water of different temperatures, e.g., 10, 30, 50, 80, and 100 C, at each temperature for 1 hour or more, starch test paper test shows no blue color, which indicates that it has a better thermal stability; there is no difference in terms of light stability and yield coefficient maintains over 85%.

Example 2: 1000 ml Liquid Atomic-State Nano-Iodine's Preparation and Test

Preparation:

Put 100 ml 70% ethanol solution into a 250 ml flask and add with 10 ml of the fluid iodine obtained in Example 1, stir at room temperature for 30 minutes, after being completely dissolved, pour it into a package bottle, then take 1 mL of the solution and dissolve it into 500 ml distilled water, shake for dispersion and filter into package bottle by a quantitative filter paper, through which the liquid atomic-state nano-iodine is obtained, it is stable at 4-20 C; centrifugalize the liquid nano-iodine at a speed of 3000-5000 rpm at low temperature for 5 minutes and the obtained solid stored at 4-8 C, which becomes the solid atomic-state nano-iodine.
Product Test Use Malvern laser particle size analyzer z-90 to measure hydrous particle diameter of the nano-iodine solution obtained in the above example and find that iodine exists in the form of nano particle with a diameter of 100-300 nm in water (as shown in FIG. 3).

Figure 4:
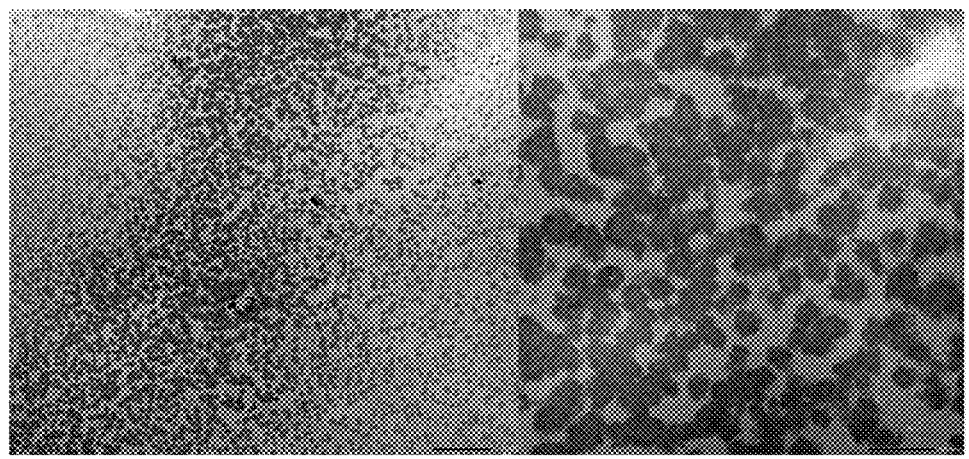

Drop the nano-iodine solution onto the copper mesh with carbon film, after drying, use JEM-1400 dry particle size analyzer made by JEOL to test and find that iodine exists in the form of nano particle with an average diameter of 100 nm in the air medium (as shown in FIG. 4).

From the two tests we can see that iodine forms nano particles, with uniform diameter and good dispersity.

Parallel Examples

In some parallel tests of this example, 80% ethanol, methanol, acetone, ethylene glycol, propylene glycol, polyvinyl alcohol or polyethylene glycol are used to replace 70% ethanol, and no significant difference is found among nano-iodine solutions obtained.

Example 3: 200 Grams Atomic-State Fluid Iodine's Preparation and Test

Material:
Iodine: Specifications: Solid, AR250 g/Bottle, Purchased from Tianjin Chemical Reagents Store
Remaining are ordinary chemical pure grade reagents.
Preparation Steps:

Put 250 g solid iodine into a 2000 ml round-bottom flask and add 1000 ml dimethyl sulfoxide, heat to 184 C by oil bath, stir for reflux distillation for 4 hours and obtain 800 ml liquids, lower-layer of which needs to be separated in delivery flask after being cooling to room temperature put the separated lower-layer liquid into washing bottle, wash it with 10 C distilled water for 5 times, and then wash with petroleum ether for 3 times, cool it to 5 C, and remove the upper liquid after solidification; under room temperature, the solid will melt into fluid, i.e. the atomic-state fluid iodine, which shall be poured into package bottle for storage. The yield coefficient stands at over 90%.
Product Test
Light and Thermal Stability Test:

Sunlight is used for light stability test: put 10 g fluid iodine into a 100 ml transparent glass bottle, with a daily sunshine of 6 hours to observe the fluid iodine overflow, if after 10 days no red material appears on the bottle wall, it turns out to possess good light stability.

Water bath is used for thermal stability test: put 10 g fluid iodine into a 100 ml transparent glass bottle, place the open bottle in 10-100 C constant temperature water, staying in water stayed in water of different temperatures, e.g., 10, 30, 50, 80 and 100 C, at each temperature for 1 hour or more, then being tested by starch test paper. If no blue color appears, the result indicates good thermal stability.

Test result shows that: the specific gravity for atomic-state fluid iodine stands at 3.8-4.0 g/ml, it exists at fluid state and possesses stable physical condition at 10-100 C and light condition, and no iodine gas overflow is detected.

Parallel Examples

In some parallel examples, diphenyl sulfone, triethanolamine, N-methylpyrrolidone, sulfolane or N, N-dimethylformamide is used as solvent instead of dimethylsulfoxide, and results of Light and thermal stability test for products obtained are consistent with abovementioned examples.

In other parallel examples, the lower-layer liquid is washed with carbon tetrachloride and dichloroethane instead of petroleum ether. The results of light & thermal stability test for products obtained are consistent with abovementioned example.

Then in other parallel examples, temperatures for oil bath are set as 110, 120, 125, 130, 135, 140, 145, 150, 155, 160, 165, 170, 175, 180, 185, 195, and 200 C respectively.

The results show that along with temperature for oil bath rising from 110 to 150 C, the stability of the products obtained gradually increases, and the yield coefficient also gradually increases from 50% to about 70%, the product was stayed in water of different temperatures, e.g., 10, 30, 50, 80 and 100 C, at each temperature for over 40 minutes, then tested by starch test paper. The test shows blue, which means that thermal stability of product obtained under such conditions is weaker than that under 185 C. There is no difference in terms of light stability.

The product obtained through 160-200 C reflux distillation method was stayed in water of different temperatures, e.g., 10, 30, 50, 80 and 100 C, at each temperature for 1 hour or more, and tested by starch test paper. The test shows no blue color, which proves that it has better thermal stability, there is no difference in terms of light stability, and yield coefficient maintains over 80%.

Example 4: Preparation and Test of 1000 ml 10% Atomic-State Nano-Iodine Parent Solution Put 900 mL 70% ethanol solution into a 2000 mL flask, and add with 100 mL of the fluid iodine obtained in example 1 or 3 with stirring at the same time, then stir at room temperature for 30 minutes, after being completely dissolved, pour it into a package bottle for storage.
Product Test:

Particle measurement steps: Instruments and test methods are same as that described in Example 2.

Test results show that iodine exists in the form of nano particle with a diameter of 100-300 nm in water, and in the form of nano particle with an average diameter of 100 nm in the air medium.

Parallel Example 4

In some of parallel tests of this example, 80% ethanol, methanol, acetone, ethylene glycol, propylene glycol, polyvinyl alcohol or polyethylene glycol is used to replace 70% ethanol, and no significant difference is found among nano-iodine solutions.

Application Example 1: Prevention and Cure of Citrus Huanglongbing by Atomic-State Fluid Iodine and Nano-Iodine This application example is carried out as following:
The experiment is carried out in Zhuliao district and Jiangmen district of Guangdong province, and atomic-state fluid iodine and 10% atomic-state nano-iodine parent solution are used to prevent and cure Citrus Huanglongbing and citrus bacterial canker disease through injection & slow release method combined with spraying method.

Operating steps for injection & slow release method go as following: through PCR molecular detection technology, select trees infected with Citrus Huanglongbing and adult trees with obvious symptoms by morphological observation, as well as 4-5 surrounding trees, as targets for preventing and curing, then select one point on trunk 30 cm or so from the ground and use a driller to bore a downward embedding hole of 0.5 cm diameter and 8-10 cm depth (until reaching the trunk center) at an angle of 45° against the truck, and inject 5 mL fluid iodine by a syringe into the hole, and seal the embedding hole with carrier material, then seal the cut by sealing compound successively; injection shall be done every 30 days, and from May to August, immunization treatment shall be applied, at the same time measure dynamic changes of pathogenic bacteria quantity in different positions of the trees through PCR detection, and physiological immune activity measurement shall also been done simultaneously.

Operating steps for spraying method go as following: dilute the 10% atomic-state nano-iodine parent solution with water to 500-3000 times then select 4-5 trees infected with Citrus Huanglongbing (the same trees selected to apply injection and slow release method), spray solution onto leaves of the citrus trees for 3-5 times, at interval of 7-10 days; then check the prevention and cure conditions through PCR molecular detection technology.

Figure 2:
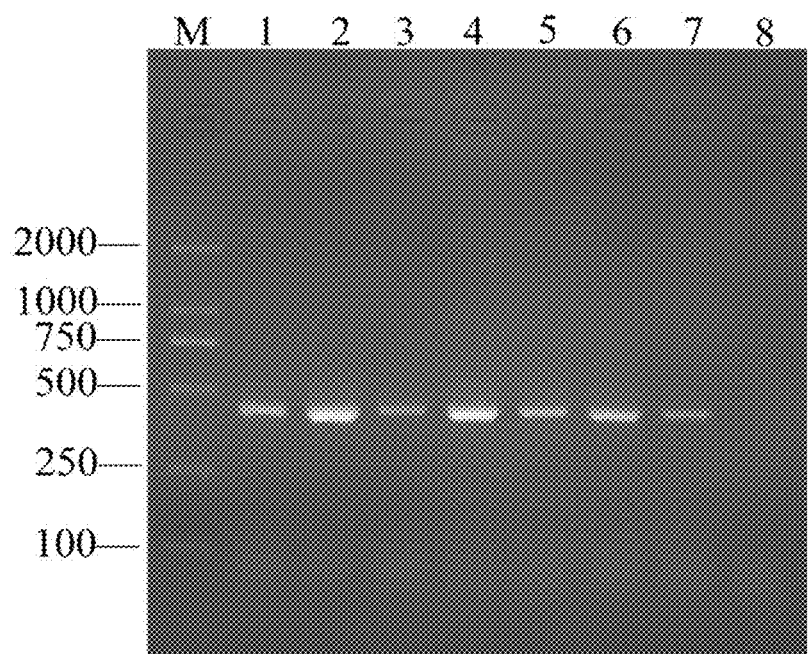

Results in FIG. 1 and FIG. 2 show that the atomic-state fluid iodine combined with atomic-state nano-iodine can kill the pathogenic bacteria of Citrus Huanglongbing.

Application Example 2: Prevention and Cure of Tomato Yellow Leaf Curl Virus Disease by Atomic-State Nano-Iodine This application example was carried out in the experimental area of Beipiao Municipal Agricultural Bureau of Liaoning Province, five greenhouses, each of which covers an area of 0.0667 hectares (1μ), have been selected, with two of them used as control groups, initially dilute the 10% atomic-state nano-iodine parent solution with water to 2000 times. The diluted solution was sprayed onto tomato leave three times respectively on Sep. 20, Sep. 28, and Oct. 3, 2017, and fresh water was sprayed to control groups; disease index of infected trees should be follow and research, and disease control rate (%)=(1−disease index of treated plants/disease index of control groups)×100%.

Results show that average disease control rate is over 70%.

Application Example 3: Disinfection Effect of Atomic-State Nano-Iodine

Method: according to national test standard for disinfectant functions, use 10% atomic-state nano-iodine solution to conduct a disinfection experiment on human hand skin, based on the experiment, disinfection effect on skin surface of atomic-state iodine is shown in the following table:

Disinfection Experiment on Human Skin Surface of Atomic-State Nano-Iodine

| Experiment No. | Bacterial count before disinfection (cfu/cm$^2$) | Bacterial count after disinfection (cfu/cm$^2$) | Kill rate | Bacterial count before disinfection (cfu/cm$^2$) | Bacterial count after disinfection (cfu/cm$^2$) | Kill rate |
|---|---|---|---|---|---|---|
| 1 | $6.51 \times 10^2$ | 1 | 99.84 | $7.19 \times 10^2$ | 1 | 99.86 |
| 2 | $6.85 \times 10^2$ | 2 | 99.70 | $4.81 \times 10^2$ | 2 | 99.58 |
| 3 | $5.50 \times 10^2$ | 0 | 100.00 | $3.55 \times 10^2$ | 3 | 99.14 |
| 4 | $4.30 \times 10^2$ | 0 | 100.00 | $4.30 \times 10^2$ | 0 | 100.0 |
| 5 | $4.08 \times 10^2$ | 2 | 99.50 | $5.60 \times 10^2$ | 0 | 100.0 |
| 6 | $2.88 \times 10^2$ | 1 | 99.64 | $5.05 \times 10^2$ | 1 | 99.80 |
| 7 | $1.31 \times 10^2$ | 1 | 99.23 | $2.22 \times 10^2$ | 1 | 99.54 |
| 8 | $3.19 \times 10^2$ | 3 | 99.06 | $5.46 \times 10^2$ | 0 | 100.0 |
| 9 | $4.06 \times 10^2$ | 0 | 100.00 | $4.77 \times 10^2$ | 0 | 100.0 |
| 10 | $4.83 \times 10^2$ | 2 | 99.58 | $1.99 \times 10^2$ | 0 | 100.0 |
| 11 | $1.91 \times 10^2$ | 2 | 98.94 | $4.61 \times 10^2$ | 3 | 99.34 |
| 12 | $5.20 \times 10^2$ | 0 | 100.00 | $2.82 \times 10^2$ | 2 | 99.28 |
| 13 | $4.71 \times 10^2$ | 3 | 99.36 | $3.21 \times 10^2$ | 1 | 99.68 |
| 14 | $7.06 \times 10^2$ | 2 | 99.71 | $5.59 \times 10^2$ | 2 | 99.55 |
| 15 | $6.22 \times 10^2$ | 1 | 99.83 | $5.85 \times 10^2$ | 0 | 100.0 |
| Average | | | 99.76 | | | |

Negative control: No bacteria grow in diluent and culture medium.

Experiment results show that: bacteria kill rate of atomic-state nano-iodine stands at 99.76%.

Application Example 4: Sterilizing Effect of 10% Atomic-State Nano-Iodine

Material:

Tested atomic-state nano-iodine: 10% atomic-state nano-iodine with 500 times dilution and 1000 times dilution.

Bacteria: according to national test standard for disinfectant effect, prepare bacterial suspensions of *Escherichia coli* and *Staphylococcus aureus*.

Method:

It is accordance with test standard for disinfectant sterilizing effect.

Results are shown as following table:

| Bacteria class | Dilutability | Average kill rate and scope (%) under different durations (min) | | | | Average control bacterial count |
|---|---|---|---|---|---|---|
| | | 1 | 3 | 5 | 7 | |
| escherichia coli | 1/500 | 99.95 (99.92-99.98) | 99.94 (99.91-99.97) | 99.95 (99.93-99.97) | 99.99 (99.99-100) | 3.98 × 10$^6$ |
| | 1/1000 | 98.54 (98.50-98.58) | 99.48 (99.38-99.55) | 99.70 (99.64-99.76) | 99.85 (99.80-99.90) | |
| staphylococcus aureus | 1/500 | 99.96 (99.94-99.99) | 99.99 (99.99-100) | 99.99 (99.99-100) | 99.99 (99.99-100) | 3.54 × 10$^6$ |
| | 1/1000 | 93.55 (92.54-94.57) | 95.45 (95.17-95.85) | 97.67 (97.49-97.79) | 96.96 (96.95-96.97) | |

Kill rate of 10% atomic-state nano-iodine with 500 times dilution towards *Escherichia coli* and *Staphylococcus aureus* is 99.96% and 99.98% respectively.

Kill rate of 10% atomic-state nano-iodine with 1000 times dilution towards *Escherichia coli* and *Staphylococcus aureus* are 99.39% and 95.90% respectively.

The above examples are merely illustrations of certain mode of executions of this invention and are not intended to limit the scope of this invention, and any modification and improvement of the technical solutions of this invention without going beyond the spirit of this invention taken by other persons engaged in this field shall fall into the scope of protection as defined in the claims of this invention.

The invention claimed is:

1. A method for producing an atomic-state fluid iodine, the method comprising proceeding following steps in a pseudo-critical reaction system, that is, ordinary pressure and temperature scope close to iodine's boiling point,
   (1) dispersing and mixing solid iodine in solvent, then stirring and refluxing under about 110 to about 200 C, cooling liquid distillate produced through said refluxing to room temperature, thereafter separating lower-layer liquid in a delivery flask, wherein said solvent selected from the group consisting of dimethyl sulfoxide, diphenyl sulfone, triethanolamine, N-methylpyrrolidone, sulfolane and N, N-dimethylformamide,
   (2) purifying: washing the lower-layer of liquid with distilled water and non-polar solvent to remove water-soluble and ester-soluble substances produced by solvent decomposition, and
   (3) placing the purified lower-layer liquid in a low temperature environment under 10 C till solidifying, thereafter removing the upper-layer solution and obtaining solid product, placing said solid product in a room temperature environment till the solid product turning into fluid, which is the atomic-state fluid iodine.

2. The method according to claim 1, wherein in step (1), said solid iodine being mixed with the solvent with the ratio of 0.1-1.0 g:1.0 ml.

3. The method according to claim 1, wherein in the step (1), stirring and refluxing at a temperature of 110 to 200 C for 3-5 hours.

4. The method according to claim 1, wherein in step (2), washing the lower-layer of liquid with distilled water and non-polar solvent for 3-8 times, then with non-polar solvent for 3-5 times.

5. The method according to claim 1, wherein, the temperature range of the distilled water is from 10 to 20 C, and the non-polar solvent is selected from the group consisting of petroleum ether, carbon tetrachloride and dichloroethane.

6. The method according to claim 1, wherein the low temperature environment described in step 3 indicates temperature below 8 C.

7. The method according to claim 1, wherein in the step (1), stirring and refluxing at a temperature of 180 to 200 C for 3-5 hours.

8. The method according to claim 1, wherein in the step (1), stirring and refluxing at a temperature of 160 to 200 C for 3-5 hours.

* * * * *